United States Patent [19]

Thompson et al.

[11] Patent Number: 4,981,609
[45] Date of Patent: Jan. 1, 1991

[54] COMPOUNDS CONTAINING SULFUR AND AMINO GROUPS

[75] Inventors: Neil E. S. Thompson, Creve Coeur; Derek Redmore, Webster Groves; Bernardus A. Oude Alink, St. Louis; Benjamin T. Outlaw, Webster Groves, all of Mo.

[73] Assignee: Petrolite Corporation, St. Louis, Mo.

[21] Appl. No.: 275,607

[22] Filed: Nov. 25, 1988

Related U.S. Application Data

[60] Division of Ser. No. 792,623, Oct. 25, 1988, Pat. No. 4,843,176, which is a continuation of Ser. No. 464,523, Feb. 7, 1983, abandoned, which is a continuation-in-part of Ser. No. 320,144, Nov. 10, 1981, abandoned, which is a division of Ser. No. 161,098, Jun. 19, 1980, Pat. No. 4,332,967.

[51] Int. Cl.$^5$ .............................................. C23F 11/10
[52] U.S. Cl. ...................................... 252/391; 422/12; 422/16
[58] Field of Search ..................... 252/391; 422/12, 16; 564/292, 285, 440, 501

[56] References Cited

U.S. PATENT DOCUMENTS

| | | | |
|---|---|---|---|
| 3,574,755 | 4/1971 | McConnell | 564/504 X |
| 3,755,176 | 8/1973 | Kinney et al. | 252/391 X |
| 3,759,956 | 9/1973 | Stapp | 252/406 X |
| 3,968,218 | 7/1976 | Bouillon et al. | 564/501 X |
| 3,968,315 | 7/1976 | Hochreuter | 564/292 X |
| 4,196,217 | 4/1980 | Rancurel et al. | 564/501 X |
| 4,332,967 | 6/1982 | Thompson et al. | 252/391 X |
| 4,450,137 | 5/1984 | Thompson et al. | 252/391 X |
| 4,673,436 | 6/1987 | Haslegrave et al. | 252/391 X |
| 4,843,176 | 6/1989 | Thompson et al. | 252/391 X |
| 4,859,354 | 8/1989 | Phillips et al. | 252/391 X |

*Primary Examiner*—John S. Maples
*Assistant Examiner*—Valerie D. Fee
*Attorney, Agent, or Firm*—Stanley M. Tarter

[57] ABSTRACT

This invention relates to the following:
(1) An amino-containing composition characterized by polymercapto groups,
(2) A polyamino-containing composition characterized by mercapto or polymercapto groups,
(3) A composition characterized by the presence of
   A. a mercapto or polymercapto groups, and
   B. a nitrogen-containing group characterized by at least one of the following:
      1. an amido or a polyamido group,
      2. a cyclic amidine or a polycyclic amidine group,
      3. an epihalohydrin-derived amino-containing group.

This invention also relates to the use of the above compositions as corrosion inhibitors.

9 Claims, No Drawings

COMPOUNDS CONTAINING SULFUR AND AMINO GROUPS

This application is a divisional application of U.S. patent application Ser. No. 792,623, filed Oct. 25, 1985; which is a Continuation-in-Part application of Application Serial No. 320,144 filed Nov. 10, 1981, which is a Divisional Application of Application Ser. No. 161,198 filed June 19, 1980, now U.S. Pat. No. 4,332,967 issued June 1, 1982.

This invention relates to compositions containing both sulfur and amino groups and to the use thereof as corrosion inhibitors.

The following patents illustrate various patents containing sulfur and/or amino groups which are employed as corrosion inhibitors. Sulfur containing, e.g. 3,809,655, 3,759,956, 3,755,176, 3,158,476, 2,880,180, 3,404,094, 3,197,403, 3,969,414. Nitrogen containing, e.g., 3,445,441, 3,450,646; sulfur and amino containing, e.g. 3,414,521.

We have now discovered compositions containing both sulfur and amino groups, which are useful as corrosion inhibitors. This invention relates to sulfur-containing corrosion inhibitors which are further enhanced by including amino-containing groups in the same molecules; and to amino-containing corrosion inhibitors which are further enhanced by including sulfur-containing groups in the same molecule. The presence of both sulfur-containing and amino-containing groups synergistically enhances the total effect as corrosion inhibitors.

The sulfur group may be any group effective in inhibiting corrosion, such as the thioether group (—S—) etc.; and the amino group may be any group effective in inhibiting corrosion such as cyclic amidine groups, for example imidazolenes, tetrahydropyrimidines, etc., non-cyclic amino groups such as amido amines, quaternary amino-groups, etc., combinations thereof, etc.

In general, the thio group is introduced by any suitable reaction. One method comprises adding a mercaptan across an unsaturated bond

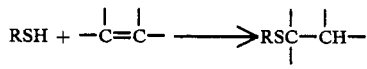

R is any group that does not interfere with the addition of the mercaptan across the unsaturated group. R may be, for example, a hydrocarbon group such as alkyl, aryl, aralkyl, cycloalkyl, etc., including substituted derivatives thereof.

The addition of mercaptan to the unsaturated groups can be accomplished with or without catalysts. Preferred catalysts include bases such as hydroxides, alkoxides, tertiary amines, etc., or catalysts which can generate radicals.

Examples of unsaturated compositions include the following:

1. The acrylate-type compounds, for example the following formula:

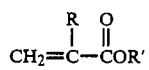

where R is for example hydrogen or an alkyl group, such as methyl, and R' is hydrogen or an alkyl group, capable of being removed so as to form an amido group, for example methyl, ethyl, propyl, isopropyl, butyl, sec-butyl, tert-butyl, aryl, hexyl, etc. In the preferred embodiments these compounds are acrylic and methacrylic esters such as methyl or ethyl acrylate, methyl or ethyl methacrylate.

2. Acrylonitriles or derivatives thereof such as

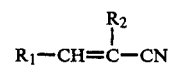

where $R_1$ and $R_2$ are H or hydrocarbon groups such as alkyl, e.g., methyl, ethyl, propyl, butyl, pentyl, etc., for example, methacrylonitrile, ethacrylonitrile, 2-methyl-2-butenenitrile, 2-pentenenitrile.

The following are illustrative.

A. One type of composition involves the reaction of thiols with unsaturated carboxylic acid esters followed by reactions with polyamines as illustrated by the following equations:

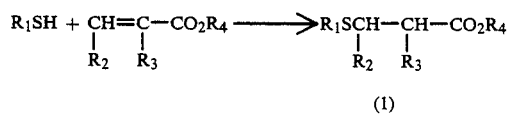

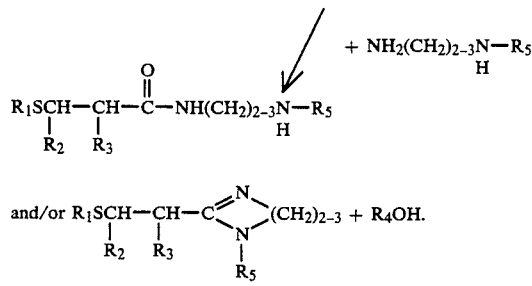

$R_1$ can be any suitable moiety such as a hydrocarbon or a substituted hydrocarbon group, for example alkyl, cycloalkyl, aryl, aralkyl, alkaryl, such as methyl, ethyl, propyl, butyl, hexyl, octyl, decyl, dodecyl, phenyl, tolyl, etc. The alkyl group may be straight chain or branched.

$R_2$ and $R_3$ can be hydrogen or alkyl such as methyl, ethyl, propyl, etc. but preferably hydrogen or methyl.

$R_4$ can be any ester moiety such as a hydrocarbon moiety, for example methyl, ethyl, butyl, hexyl, decyl, dodecyl, octadecyl, etc. but preferably methyl or ethyl.

$R_5$ can be H, alkyl, alkanol, aryl, aralkyl, cycloalkyl,

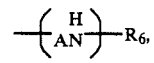

where A is alkylene capable of forming a cyclic amidine ring and $R_6$ is H or a hydrocarbon group such as alkyl, etc.

The addition is carried out at any suitable temperature. Temperatures up to the decomposition points of reactants and products such as up to 200° C. or higher have been employed. In practice, one generally carries out the condensation by heating the reactants below 100° C., such as 80°–90° C. for a suitable period of time, such as a few hours. Where an acrylic-type ester is employed, the progress of the reaction can be judged by the removal of the alcohol in forming the amide. During the early part of the reaction alcohol is removed quite readily below 100° C. in the case of low boiling alcohols such as methanol or ethanol. As the reaction slows, the temperature is raised to push the condensation to completion and the temperatures may be raised to 150°–200° C. toward the end of the reaction. Removal of alcohol is a convenient method of judging the progress and completion of the reaction which is generally continued until no more alcohol is evolved. Based on removal of alcohol, the yields are generally stoichiometric.

The reaction time involved can vary widely depending on a wide variety of factors. For example, there is a relationship between time and temperature. In general, lower temperature demands longer times. In practice we employ times of from about 2 to 30 hours, such as 5 to 25 hours, and preferably 3 to 10 hours.

We have found that although one can employ a solvent, the reaction can be run without the use of any solvent. In fact, where a high degree of cross-linking is desired, it is preferable to avoid the use of a solvent and most particularly to avoid a polar solvent such as water. However, taking into consideration the effect of solvent on the reaction, where desired, any suitable solvent can be employed, whether organic or inorganic, polar or non-polar.

One embodiment relates to compositions where the mole ratios of the unsaturated esters to thiol are greater than 1, such as 2:1, 3:1, 4:1, etc. These products are polymeric aminoamides with attached thio groups represented by the following idealized formula. They are in essence the composition of U.S. Pat. No. 3,445,441 modified with thio group.

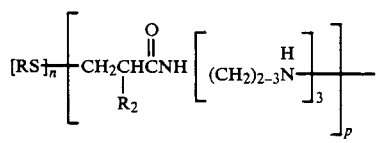

These thioethers (1) can be prepared by other methods such as

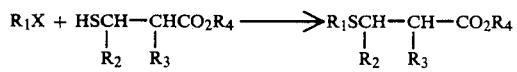

where X is halogen, Cl, Br, I, etc.

B. A second type of composition involves the reaction of thiols with unsaturated nitriles followed by reaction with polyamines.

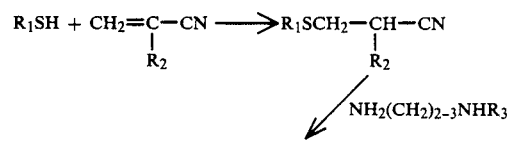

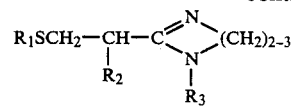

$R_3$ is H, alkyl, aryl, alkaryl, aralkyl, cycloalkyl, alkanol

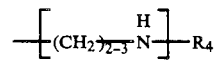

$R_4$ is hydrocarbon group such as alkyl, etc.

The addition of mercaptan to unsaturated nitrile can be carried out with or without catalyst but it is generally preferred to use a basic catalyst such as an alkali metal hydroxide, alkoxide or a quaternary ammonium hydroxide.

The cyanoethylated thiol or mixtures of cyanoethylated thiol and cyanoethylated polyamine is reacted with a polyamine under cyclic amidine-forming conditions to form the polymer of this invention. Although the reaction may proceed without a catalyst it is preferable that a catalyst be employed to speed up the reaction. Among such catalysts are organic and inorganic salts such as sulfonic acids, etc. However, it is preferred to use sulfur compounds such as $H_2S$, thioacids, thioamides, thioketones, thiourea, dithiobiuret, etc., as catalysts.

A very useful embodiment involves the use of a mole ratio of unsaturated nitrile to thiol of greater than 1:1, e.g. 2:1, 3:1, 4:1, etc. The product is a polyamidine modified by thio groupings of the general idealized formula:

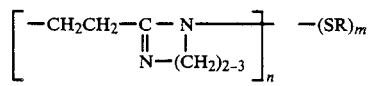

These compositions are in essence the compositions of U.S. Pat. No. 3,450,646 modified with thio groups, C. A third type of composition is derived from thioglycolic acid derivatives and amines according to the formula

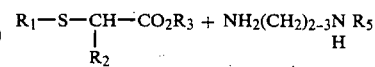

(2)

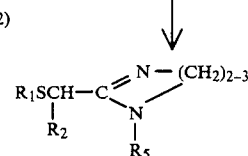

and/or

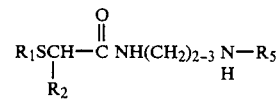

The condensation step can be carried out without or with solvent at temperatures from 60°–200° C. but preferably from 80°–150° C.

The thioglycolic acid derivatives (2) can be prepared by various routes such as shown in equations (1) and (2):

Equation 1

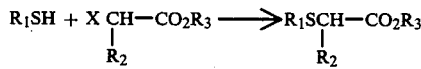

$$R_1SH + X\underset{R_2}{\overset{|}{CH}}\text{—}CO_2R_3 \longrightarrow R_1S\underset{R_2}{\overset{|}{CH}}\text{—}CO_2R_3$$

where X is halogen, Cl, Br, I etc.

Equation 2

$$R_1X + HS\underset{R_2}{\overset{|}{CH}}\text{—}CO_2R_3 \longrightarrow R_1S\underset{R_2}{\overset{|}{CH}}\text{—}CO_2R_3$$

where X is halogen, Cl, Br, I.

D. A fourth type of compositions of this invention involves the reaction of thiols with epichlorohydrin followed by reaction with amines or polyamines illustrated by the following equation:

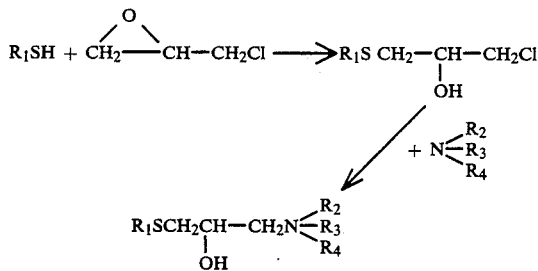

R$_1$ is the group as defined above.
R$_2$, R$_3$ and R$_4$ can be H, alkyl, cycloalkyl, aryl, aralkyl, alkaryl, or alkylamino for polyalkylane such as

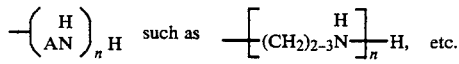

The reaction step between thiol and epichlorohydrin can be carried out with or without solvent and with or without catalyst. It is generally preferred to use a solvent such as an alcohol (e.g. isopropanol, butanol) and a basic catalyst such as a tertiary amine.

The following examples are presented by way of illustration and not of limitation.

A. Products derived from alkylthiols, unsaturated esters and amines

EXAMPLE 1

In a flask, fitted stirrer, condenser, thermometer, and addition funnel was placed octyl thiol (36.5g; 0.25 mole) and Triton B (5 drops, catalyst) was added. To this thiol, methyl methacrylate (25g; 0.25 mole) was added dropwise while stirring at a rate such that the temperature was maintained between 50° and 60° C. After stirring for 1 hour the addition reaction of the thiol to the methacrylate was complete. Infrared analysis showed the absence of thiol SH and unsaturated ester function an presence of saturated ester. (1740cm$^{-1}$). To this thioether was added diethylene triamine (26g; 0.25 mole) and the mixture heated to 185°-195° C. As the temperature reached 180° methanol began to be liberated and distillation was continued for 1-1½ hrs. during which time 8 g of distillate was collected (0.25 mole The product (80 g) was a yellow viscous liquid soluble in aqueous alcohol and water dispersable.

Analysis gave: N, 13.20%; S, 10.15%. (calculated: N, 13.25%; S, 10.09%)

Infrared analysis showed C=O 1650 cm$^{-1}$ (amide).

The product has the following structure:

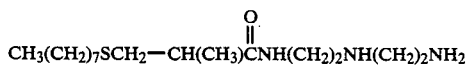

$$CH_3(CH_2)_7SCH_2\text{—}CH(CH_3)\overset{O}{\overset{\|}{C}}NH(CH_2)_2NH(CH_2)_2NH_2$$

EXAMPLE 2

To dodecylthiol (40 g; 0.2 mole) containing 5 drops of Triton B was slowly added methyl methacrylate (20 g; 0.2 mol so that the temperature was kept below 60° C. After heating for 1 hr. at 50°-60° the reaction between thiol and methacrylate was complete. After cooling to room temperature diethylene triamine (20 g; 0.2 mole) was added and the mixture heated to 180°. Methanol formed in the condensation was allowed to distill from the reaction and was collected (6 g). The product was an amber viscous liquid dispersible in water. Infrared analysis showed C=O 1650 cm$^{-1}$ (amide). The product has the following structure:

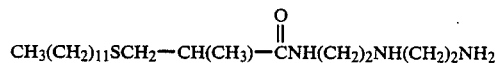

$$CH_3(CH_2)_{11}SCH_2\text{—}CH(CH_3)\text{—}\overset{O}{\overset{\|}{C}}NH(CH_2)_2NH(CH_2)_2NH_2$$

EXAMPLE 3

This example uses the same reactants as Example 1, but in different ratios.

To octyl thiol (14.6 g; 0.1 mole) containing 5 drops of Triton B as catalyst was added methyl methacrylate (40 g; 0.4 mole) dropwise during 45 mins. After stirring for an additional 1 hr. infrared analysis showed the absence of thiol SH and the presence of both saturated and unsaturated ester groups (1740 cm$^{-1}$ and 1725 cm$^{-1}$). To this mixture diethylene triamine (41.2 g; 0.4 mole) was added and the mixture heated with stirring. As the reaction temperature reached 160° methanol was formed and removed by distillation. After heating at 180°-185° for 1 hour 13 g of methanol distillate had been collected leaving 75 g of a yellow viscous product. The product was readily water soluble Infrared analysis showed C=O 1650cm$^{-1}$ (amide) and no residual ester groups: The product is an oligomeric amino-amide containing thioether groups Analysis: Found N, 20.96; S, 3.97. Calculated: N, 20.24; S, 3.85.

EXAMPLE 4

This example illustrates the use of a different amine.

To octylthiol (30 g; 0.2 mole) containing Triton B (5 drops) as catalyst was added methyl methacrylate (20 g; 0.2 mole dropwise during 1 hour at 50°-60°. After stirring 1 hour at 60° aminoethylethanolamine (21 g; 0.2 mole) was added and the mixture heated at 170°-185° for 1½ hrs. After this time distillation of methanol ceased leaving the product as a yellow viscous liquid dispersible in water. The product is represented by the following structure:

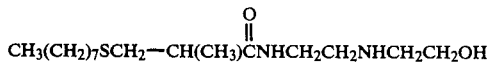

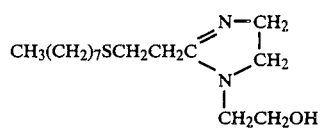

The following table lists additional examples prepared by the method of Example 1

TABLE 1

| Example Number | Ester (moles) | Thiol (moles) | Amine (moles) |
|---|---|---|---|
| 5 | Methyl methacrylate (0.4) | Octylthiol (0.2) | Diethylene Triamine (0.4) |
| 6 | Methyl methacrylate (0.4) | Octylthiol (0.05) | Diethylene Triamine (0.4) |
| 7 | Methyl methacrylate (0.2) | Dodecylthiol (0.1) | Diethylene Triamine (0.2) |
| 8 | Methyl methacrylate (0.4) | Dodecylthiol (0.05) | Diethylene Triamine (0.4) |
| 9 | Methyl methacrylate (0.4) | Dodecylthiol (0.2) | Aminoethylethanolamine (0.4) |
| 10 | Methyl methacrylate (0.4) | Dodecylthiol (0.025) | Ethylenediamine (0.4) |
| 11 | Methyl Acrylate (0.4) | Dodecylthiol (0.05) | Diethylene Triamine (0.4) |
| 12 | Methyl Acrylate (0.4) | Dodecylthiol (0.025) | Ethylene diamine (0.4) |
| 13 | Methyl methacrylate (0.25) | Octylthiol (0.2) | Ethylene diamine (0.25) |
| 14 | Methyl methacrylate (0.4) | Octylthiol (0.2) | Aminoethylethanolamine (0.4) |
| 15 | Methyl Acrylate (0.4) | Octylthiol (0.05) | Aminoethylethanolamine (0.4) |
| 16 | Methyl Acrylate (0.4) | Octylthiol (0.05) | Diethylene triamine (0.4) |
| 17 | Methyl Acrylate (0.4) | Octylthiol (0.05) | Ethylene diamine (0.4) |

B. Products derived from alkyl thiols, unsaturated nitrile and amines.

The following table lists additional examples prepared by the method of Example 19.

TABLE 2

| Example Number | Nitrile (moles) | Thiol (moles) | Amine (moles) |
|---|---|---|---|
| 20 | Acrylonitrile (0.4) | Dodecylthiol (0.2) | Aminoethylethanolamine (0.4) |
| 21 | Acrylonitrile (0.4) | Dodecylthiol (0.2) | Diethylene triamine (0.4) |
| 22 | Acrylonitrile (0.75) | Dodecylthiol (0.05) | Ethylene diamine (0.67) |
| 23 | Acrylonitrile (0.4) | Dodecylthiol (0.05) | Diethylene triamine (0.4) |
| 24 | Acrylonitrile (0.4) | Octylthiol (0.27) | Diethylene triamine (0.4) |
| 25 | Acrylonitrile (0.4) | Octylthiol (0.05) | Aminoethylethanolamine (0.4) |
| 26 | Acrylonitrile (0.4) | Octylthiol (0.05) | Ethylene diamine (0.4) |

EXAMPLE 18

To octyl thiol (27 g; 0.18 mole) was added acrylonitrile (12 g; 0.23 mole) at less than 60° C. After the addition the reaction mixture was maintained at 55°-60° for 1 hour. Infrared analysis showed the absence of thiol-SH and vinyl unsaturation. To this mixture was added diethylene triamine (24 g; 0.23 mole) and thicurea (1 g) (catalyst). Upon heating to 125° ammonia evolution commenced and after heating at 165° for 3 hours was complete. The product obtained can be represented by the following formula:

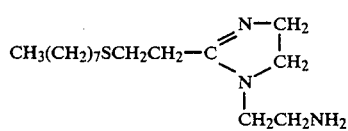

EXAMPLE 19

To octyl thiol (64 g; 0.44 mole) containing Triton B (5 drops) was slowly added acrylonitrile (30 g; 0.57 mole) during 45 mins at less than 60° C. After stirring at ambient temperature for a further 1 hour aminoethylethanolamine (60 g; 0.57 mole) and thiourea (1 g) were added. Upon heating to 135° ammonia evolution commenced and became rapid at 165°-170°. The ammonia evolution was essentially complete in 3 hours yielding a dark viscous water dispersible product. The product is represented by the following formula:

C. Products derived from alkylthioacetic acids and amines.

EXAMPLE 27

To decylthioacetic acid (46.4 g; 0.2 mole) in xylene (250 ml) was added aminoethylethanolamine (20.4 g; 0.2 moles) and the solution heated at reflux for 7 hrs. using a Dean-Stark trap to collect water (7.5 ml). Removal of solvent under vacuum gave the hydroxyethylimidazoline. The infrared spectrum showed strong C=N absorption at 1590 cm$^{-1}$. $^{13}$C nmr spectrum was also consistent with the structure as shown below:

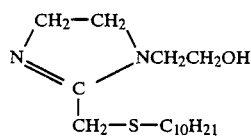

EXAMPLE 28

To tetradecylthioacetic acid (57.6 g; 0.2 mole) in xylene was added aminoethylethanolamine (20.4 g; 0.2 mole) and the solution heated at reflux with azeotropic removal of solvent condensation as in Example 27. After removal of solvent under vacuum the product was obtained showing a strong infrared absorption at 1590 cm$^{-1}$ due to imidazoline. The product is represented by the following structure:

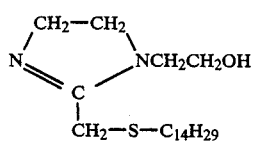

EXAMPLE 29

By the procedure of Example 27 octylthioacetic acid was reacted with aminoethylethanolamine to yield the idazoline represented by the following formula:

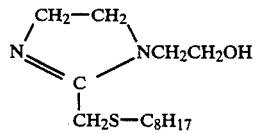

D. Products derived from thiols, epichlorohydrin and amines.

EXAMPLE 30

To a solution of octylthiol (38 g; 0.26 mole) in isopropanol (100 ml), containing 2 ml of triethylamine as catalyst, was added epichlorchydrin (24 g; 0.26 mole) dropwise at 60°-70° C. Upon completion of the addition the mixture was heated at reflux for 2 hours. To this chlorohydrin was added a $C_{12}$-$C_{14}$ alkyl dimethylamine (57 g; 0.25 mole) and the mixture heated at reflux for 12 hrs. The product is represented by the following formula:

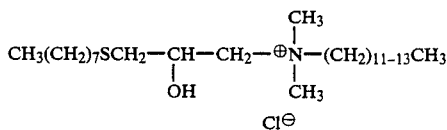

EXAMPLE 31

By a procedure similar to Example 30 octylthiol (38 g; 0.26 mole) in isopropanol (75 ml) was reacted with epichlorohydrin (24 g; 0.26 mole) to yield a chlorohydrin. this solution was added triethylamine (26 g; 0.26 mole) and the mixture heated at reflux for 12 hrs. The product is represented by the following formula:

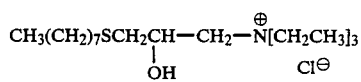

EXAMPLE 32

By the procedure of Example 30 dodecylthiol (53 g; 0.26 mole) in isopropanol (75 ml) was reacted with epichlorohydrin (24 g; 0.26 mole) to yield a chlorohydrin. To the resulting solution was added triethylamine (26 g; 0.26 mole) and the mixture heated at reflux for 12 hrs. The product obtained is represented by the formula below:

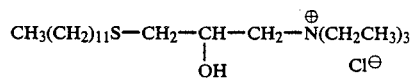

The following table lists additional examples prepared according to the method of Example 30.

TABLE 3

| Example Number | Epichlorohydrin (moles) | Thiol (moles) | Amine (moles) |
|---|---|---|---|
| 33 | Epichlorohydrin (0.2) | Dodecylthiol (0.05) | N,N-Dimethylpropylene diamine (0.2) |
| 34 | Epichlorohydrin (0.2) | Dodecylthiol (0.05) | Ethylene diamine (0.2) |
| 35 | Epichlorohydrin (0.2) | Dodecylthiol (0.05) | Diethylene triamine (0.2) |
| 36 | Epichlorohydrin (0.26) | Octylthiol (0.26) | Akolidine 11* (0.3) |
| 37 | Epichlorohydrin (0.07) | Dodecylthiol (0.07) | Akolidine 11* (0.1) |

*Akolidine 11 is a crude alkylpyridine mixture manufactured by Lonza.

Examples of polyamines employed herein are polyalkylenepolyamines, for example, of the formula

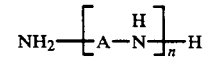

where n is an integer 1, 2, 3, 4, 5, 6, 7, 8, 9, 10, etc., and A is an alkylene group, provided that the polyamine contains an alkylene moiety of a cyclic-amidine forming group, i.e., a group having a

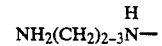

group.

One or more of the hydrogens on the $CH_2$ groups may be substituted for example, by such groups as alkyl groups, for example, methyl, ethyl, etc. Examples of A include

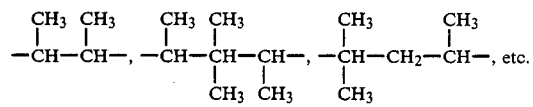

Examples of polyamines include the following ethylene diamine, propylene diamine, diethylene triamine, dipropylene triamine, triethylene tetramine, tripropylene tetramine, tetraethylene pentamine, tetrapropylene pentamine, polyalkyleneimines, i.e. the higher molecular weight amines derived from alkyleneimine such as polyethyleneimines, polypropyleneimine etc. Mixtures of the above polyamine amines and those polyamines containing both ethylene and propylene groups, for example

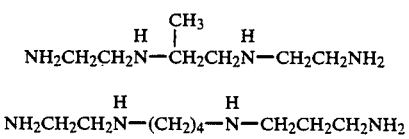

etc., can be employed.

Some of the N-groups may be substituted (provided the polyamine is cyclic-amidine forming), for example, with hydrocarbon groups such as alkyl groups, etc.

In addition, to the basic form of these compositions, one can, in certain instances, prepare salts or quaternaries, either with organic or inorganic acids or quaternizing agents such as benzyl halides, alkyl halides, etc., dihalides such as alkylene dihalide, xylylene dihalides, alkylene ether dihalides such as $(XCH_2CH_2)_2O$, etc. Being basic the cyclic amidine unit readily forms salts, including di- and polysalts.

Examples of acids which can be employed to form salts include HCl, $H_2SO_4$, $H_3PO_4$, hydrocarbon sulfonic acids, acetic acid, oxalic acid, maleic acid, oleic acid, abietic acid, naphthenic acid, rosin, benzoic acid, phthalic acid, diglycollic acid, etc.

In summary, this invention relates to compositions containing both sulfur and amino groups. Specific compositions thereof are characterized by the presence of
A. a mercapto or a polymercapto group, and
B. a nitrogen-containing group characterized by at least one of the following:
 1. an amido or a polyamido group,
 2. a cyclic amidine or a polycyclic amidine group,
 3. an epihalohydrin-derived amino-containing group.

Illustrative but non-limiting compositions include the following:

$$R_1SCH-CHC(O)N(CH_2)_{2-3}N-R_5 \quad \text{and/or} \tag{1}$$
with $R_2$, $R_3$ substituents $$R_1SCH-CH-C\underset{N(R_5)}{\overset{N}{\diagup}}(CH_2)_{2-3}$$
with $R_2$, $R_3$ substituents where
R$_1$ is a hydrocarbon group, such as alkyl, cycloalkyl, aryl, aralkyl, alkyaryl, substituted derivatives thereof, etc.
R$_2$, R$_3$ and H or alkyl, and
R$_5$ is H, $$\text{alkyl}\!-\!\!\left[\text{Alkylene}\!-\!\overset{H}{N}\right]_n\!\!-\!H,$$

alkanol, etc.
where
n is 1 or more, for example, 1 to 10 or more, but preferably 1 to 6.

$$[R_1S]_{\overline{n}}\!\!\left[\!-CH_2CHC(O)-\overset{H}{N}\left[(CH_2)_{2-3}\overset{H}{N}\right]_m\!\right]_p \tag{2}$$
with R$_2$ substituent where
R$_1$ is a hydrocarbon group such as alkyl, cycloalkyl, aryl, aralkyl, alkaryl, substituted derivatives thereof, etc.,
n, m and p are one or more such as
where
n=1 to 50, but preferably 1 to 10
m=1-10, but preferably 1 to 6.

p=1-50, but preferably 1-20.

$$R_1SCH-CH-C\underset{N(R_3)}{\overset{N}{\diagup}}(CH_2)_{2-3} \tag{3}$$
with R$_2$ substituent where
R$_1$ is a hydrocarbon group, such as alkyl, cycloalkyl, aryl, aralkyl, alkaryl substituted derivatives thereof, etc.
R$_2$ is H or alkyl, and
R$_3$ is H, alkyl, $$-\!\!\left[\text{alkylene}\!-\!\overset{H}{N}\right]_n\!\!-H,$$

such as $$\left(-CH_2CH_2\overset{H}{N}\right)_n\!\!-H,$$

etc., alkanol such as ethanol, etc.
where
n is one or more, for example, 1-10 or more, but preferably 1 to 6.

$$RS-CH_2-CH_2-C\underset{N-(CH_2)_2CN}{\overset{N-(CH_2)_{2-3}}{\diagup}} \quad \text{and/or} \tag{4}$$

$$(RS)_n\!\!-\!\!\left[-(CH_2)_2-\underset{N}{\overset{C}{\|}}-N\underset{(CH_2)_{2-3}}{\diagdown}\right]_p$$

where
R is a hydrocarbon group such as alkyl, cycloalkyl, aryl, aralkyl, alkaryl, substituted derivatives thereof, etc.,
n and p are one or more, for example where n=1-10, but preferably 1-5 and p=1-20, but preferably 1-10.

$$R_1SCH-C(O)\overset{H}{N}\!\!-\!(CH_2)_{2-3}\overset{H}{N}-R_4 \quad \text{and/or} \tag{5}$$
with R$_2$ substituent $$R_1SCH-C\underset{N(R_4)}{\overset{N-(CH_2)_{2-3}}{\diagup}}$$
with R$_2$ substituent where
R$_1$ is a hydrocarbon group, such as alkyl, cycloalkyl, aryl, aralkyl, alkaryl substituted derivatives thereof, etc.,
R$_2$ is H, alkyl, etc.,
R$_4$ is H, alkyl, alkanol such as ethanol etc.,

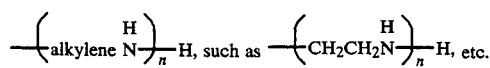

where n is one or more such as 1 to 10, but preferably 1–6.

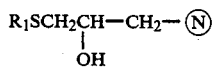 (6)

where
R$_1$ is a hydrocarbon group, such as alkyl, cycloalkyl, aryl, aralkyl, alkaryl substituted derivatives thereof, etc., and Ⓝ is an amino moiety such as where

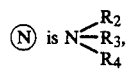

where
R$_2$, R$_3$ and R$_4$, which are the same or different, are H, alkyl, cycloalkyl, aryl, aralkyl, alkaryl,

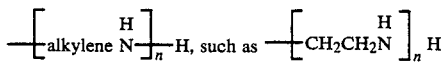

and where n is 1 or more such as 1 to 10, but preferably 1–6.

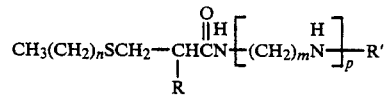 (7)

where
R=H or alkyl such as methyl, etc., R'=H or alkanol, such as —CH$_2$CH$_2$OH, etc.,
p is one or more such as 1–1, but preferably 1–6.
n is one or more such as 1–30 but preferably 1–17
m is 2–6 preferably 2–3

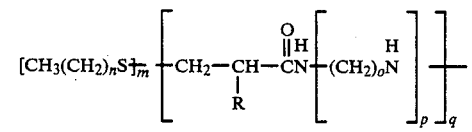 (8)

where R is H or alkyl such as methyl, etc., and one or more such as where
n=1–30, but preferably 1–17
m=1–10, but preferably 1–5
o=2–6, but preferably 2–3
p=1–10, but preferably 1 to 6
q=1–20, but preferably 1–10.

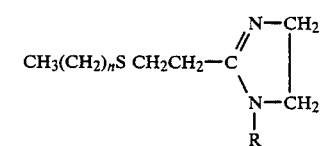 (9)

where

-continued

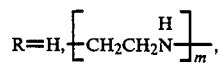

alkanol such as CH$_2$CH$_2$OH, etc.
where
m=1 to 10, but preferably 1 to 6
n=one or more such as 1 to 30, but preferably 1–17.

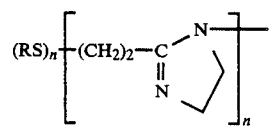 (10)

where
n and m are one or more, such as where n=1 to 10, but preferably 1 to 6, and m=1–20, but preferably 1–10

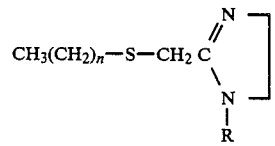 (11)

where
R is H, alkanol such as CH$_2$CH$_2$OH, etc.,

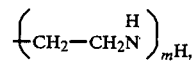

etc.
n is one or more such as 1–30, but preferably 1–17.
m is 1–10 but preferably 1–6.

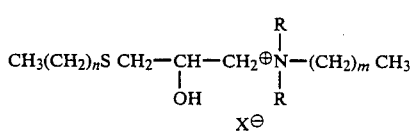 (12)

R=alkyl such as methyl, ethyl, etc., X=anion, such as halogen, for example Cl, Br, I, etc., sulfate, sulfonate, acetate, etc.
m and n=one or more, such as 1 to 30, but preferably 1–17.

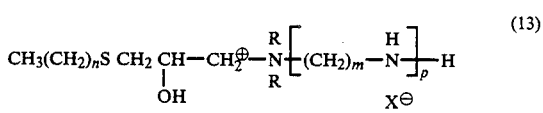 (13)

X=anion such as halogen, for example Cl, Br, I, etc., sulfate, sulfonate, acetate, etc.
R=H or alkyl such as methyl, ethyl, etc.
n is one or more, such as where n=1–30, but preferably 1 to 17,
m=2 to 6, but preferably 2 to 3, and p=1 to 10, but preferably 1 to 6.

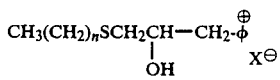

ł = pyridine or substituted pyridine, X is anion such as halogen, for example Cl, Br, I, etc., and sulfate, sulfonate, acetate, etc.

n = one or more such as 1-30, but preferably 1-17.

The molar ratios of thiols to epichlorohydrin to amines (including polyamines) can vary widely, for example as shown in the following Table:

TABLE 4

| | Molar Ratios | | |
|---|---|---|---|
| | Epichlorohydrin | Amine | Thiol |
| Broad | 1 to 0.05 | 0.05 to 1 | .05 to 0.9 |
| Intermediate | 1 to 0.5 | 0.5 to 1 | 0.2 to 0.8 |
| Preferred | 1 | 1 | 0.5 |

The method described above and illustrated by Table 4 and Examples A to G, as well as Examples 33-35 in Table 3, yield products containing the moieties $R_1S$,

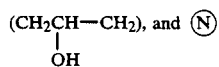

wherein $R_1$ is a hydrocarbon group and (N) is an amino moiety and where the molar ratios of

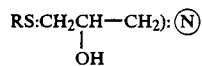

are other than 1:1:1. (N) is preferably the moiety of aminoethylethanolamine or

where $R_2$, $R_3$, and $R_4$ are H, alkyl, aryl or

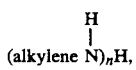

where
n is 1 or more. Most preferred are products wherein $R_1$ is $CH_3(CH_2)_n$, $R_2$ and $R_3$ are hydrogen or alkyl and $R_4$ is

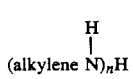

where n is 1 or more.

The preferred molar ratios of the moieties,

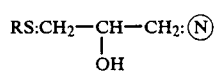

are from about 0.05 to 0.9:1 to 0.05:0.05 to 1; more preferably from about 0.2 to 0.8:1 to 0.5:0.5 to 1; and most preferably 0.5:1:1.

By varying the ratios one may enhance the corrosion inhibitor properties in various systems.

The following examples are presented for purposes of illustration and not of limitation.

EXAMPLE A

In a 1000 ml three-necked flask fitted with a stirrer, thermometer and reflux condenser was placed n-dodecylthiol (80.4 g; 0.4 mole), isopropanol (160 g) and triethylamine catalyst (4 g). The mixture was heated to reflux and epichlorohydrin (37.2 g; 0.4 mole) was added over a period of 15 minutes. The mixture was heated at reflux for an hour which gave virtually complete conversion to the 3-chloro-2-hydroxypropylthio ether. Diethylene triamine (82.4 g; 0.8 mole) was then added slowly to the above chlorohydrin at reflux. After a further 30 minutes epichlorohydrin (37.2 g; 0.4 mole) was slowly added and heating continued at reflux for 3 hours. Analysis of the resulting solution gave the following results; Nitrogen total 8.50%, Nitrogen basic 5.11%, chloride 7.62% and sulfur 3.01%.

EXAMPLE B (EXAMPLE 35)

A solution of dodecylthiol (10 g; 0.05 mole) in isopropanol (50 ml) and triethylamine (2 ml) was heated at gentle reflux and epichlorohydrin (19 g; 0.2 mole) was added dropwise during 10 minutes. After heating for an hour at reflux to complete the conversion of the thiol to chlorohydrin diethylene triamine (20.6 g; 0.2 mole) was carefully added during 15 minutes. The reaction was completed by heating at reflux for 2 hours.

EXAMPLE C

To a mixture of dodecylthiol (20.2 g; 0.1 mole) and triethylamine (2 ml) was added epichlorohydrin (19 g; 0.2 mole) dropwise at 50°-60° C. After the addition the mixture was heated at 70°-80° C. for one hour before cooling in an icebath. To the cooled chlorohydrin/thiol mixture was added a solution of diethylene triamine (20.6 g; 0.2 mole) in isopropanol (65 ml). After the addition the mixture was heated to reflux and maintained for 2 hours to complete the reaction.

EXAMPLE D

A solution of octylthiol (14.6 g; 0.1 mole) and triethylamine (2 ml) in isopropanol (35 ml) was heated to 70° C. and treated with epichlorohydrin (19 g; 0.2 mole). After the addition the reaction was continued by heating 1 hour at reflux. A solution of diethylenetriamine (20.6 g; 0.2 mole) in water (27 ml) was added and the reaction completed by heating at reflux for 2 hours.

EXAMPLE E (EXAMPLE 34)

Dodecylthiol (10 g; 0.05 mole) and triethylamine (2 ml) in isopropanol (55 ml) heated to 70° C. was treated with epichlorohydrin (19 g; 0.2 mole) dropwise during 15 minutes. After heating at reflux for 1 hour ethylenediamine (12 g; 0.2 mole) was added and heating continued for one more hour.

EXAMPLE F

According to the procedure of Example C dodecylthiol (20.2 g; 0.1 mole) was reacted with epichlorohydrin (19 g; 0.2 mole) with triethylamine (2 ml) as catalyst in isopropanol (65 ml) as solvent. The resulting chlorohydrin was then reacted with aminoethylethanolamine (20.8 g; 0.2 mole).

EXAMPLE G

By the procedure of Example C octylthiol (14.6 g; 0.1 mole) was reacted with epichlorohydrin (19 g; 0.2 mole) in presence of triethylamine (2 ml) in isopropanol (35 ml). The resulting chlorohydrin was reacted with aminoethylethanolamine (20.8 g; 0.2 mole).

Corrosion Test Results

Corrosion tests were carried out at ambient temperature in 2% sodium chloride saturated with carbon dioxide. Corrosion rates were measured using PAIR meter of the type described in U. S. Pat. No. 3,406,101. Inhibitors were injected after the electrodes had been allowed to corrode for 2 hours.

Protection is calculated in the usual manner from corrosion rate ($R_1$) of fluids without inhibitor and corrosion rate ($R_2$) in presence of particular inhibitor according to the formula:

$$[(R_1 - R_2)/R_1] \times 100 = \text{Percent protection.}$$

Blank corrosion rates under these conditions was 51 mpy.

| | Corrosion Test Data | | |
|---|---|---|---|
| | Percent Protection at Concentration | | |
| Example | 25 ppm | 50 ppm | 100 ppm |
| Example C | 84 | — | 79 |
| Example D | 84 | 80 | 83 |
| Example F | 82 | 91 | 91 |

Acid Inhibitors test in Hydrochloric Acid 200 ml of 5% hydrochloric acid in a 300 ml beaker is heated to 74° C.-77° C. and the chemical to be tested is added at the appropriate concentration. Cleaned 1020 mild steel coupons (7/8×3¼×1/6") are weighed and then placed in the acid for exactly one hour. The coupons are removed and washed with hot water, hot acetone, air dried and then re-weighed.

Corrosion protection is calculated in the usual manner from the weight loss of the blank ($W_1$) and weight loss ($W_2$) in the presence of inhibitor according to the formula $(W_1-W_2)/W_1 \times 100 =$ Percent protection.

The coupons used in corrosion experiments weighed 20.5–21 g and the typical weight loss without inhibitors was 1.3 g.

| Pickle Acid Inhibitor Tests | | |
|---|---|---|
| Compound | Concentration ppm | Protection |
| Example B | 250 | 92% |
| Example E | 250 | 94% |

The results of the above Examples are summarized in the following table:

| Ex. | Thiol | Epichlorohydrin | Amine |
|---|---|---|---|
| A | 0.5 | 1.0 | 1 |
| B | 0.25 | 1.0 | 1.0 |
| C | 0.5 | 1.0 | 1.0 |

| Ex. | Thiol | Epichlorohydrin | Amine |
|---|---|---|---|
| D | 0.5 | 1.0 | 1.0 |
| E | 0.25 | 1.0 | 1.0 |
| F | 0.5 | 1.0 | 1.0 |
| G | 0.5 | 1.0 | 1.0 |

USE AS CORROSION INHIBITORS

This phase of this invention relates to the use of these compositions in inhibiting the corrosion of metals, most particularly iron, steel and ferrous alloys. These compositions can be used in a wider variety of applications and systems where iron, steel and ferrous alloys are affected by corrosion. They may be employed for inhibiting corrosion in processes which require this protective or passivating coating as by dissolution in the medium which comes in contact with the metal. They can be used in preventing atmospheric corrosion, underwater corrosion, corrosion in steam and hot water systems, corrosion in chemical industries, underground corrosion, etc.

The corrosion inhibitors contemplated herein find special utility in the prevention of corrosion of pipe or equipment which is in contact with a corrosive oil-containing medium, as, for example, in oil wells producing corrosive oil or oil-brine mixtures, in refineries, and the like. These inhibitors may, however, be used in other systems or applications. They appear to possess properties which impart to metals resistance to attack by a variety of corrosive agents, such as brines, weak inorganic acids, organic acids, $CO_2$, $H_2S$, etc.

The method of carrying out this process is relatively simple in principle. The corrosion preventive reagent is dissolved in the liquid corrosive medium in small amounts and is thus kept in contact with the metal surface to be protected. Alternatively, the corrosion inhibitor may be applied first to the metal surface, either as is, or as a solution in some carrier liquid or paste. Continuous application, as in the corrosive solution, is the preferred method, however.

The present process finds particular utility in the protection of metal equipment of oil and gas wells, especially those containing or producing an acidic constituent such as $H_2S$, $CO_2$, organic acids and the like. For the protection of such wells, the reagent, either undiluted or dissolved in a suitable solvent, is fed down the annulus of the well between the casing and producing tubing where it becomes commingled with the fluid in the well and is pumped or flowed from the well with these fluids, thus contacting the inner wall of the casing, the outer and inner wall of tubing, and the inner surface of all wellhead fittings, connections and flow lines handling the corrosive fluid.

Where the inhibitor composition is a liquid, it is conventionally fed into the well annulus by means of a motor driven chemical injector pump, or it may be dumped periodically (e.g., once every day or two) into the annulus by means of so-called "boll weevil" device or similar arrangement. Where the inhibitor is a solid, it may be dropped into the well as a solid lump or stick, it may be blown in as a powder with gas, or it may be washed in with a small stream of the well fluids or other liquid. Where there is gas pressure on the casing, it is necessary, of course, to employ any of these treating methods through a pressure equalizing chamber equipped to allow introduction of reagent into the chamber, equalization of pressure between chamber and casing, and travel of reagent from chamber to well casing.

Occasionally, oil and gas wells are completed in such a manner that there is no opening between the annulus and the bottom of the tubing or pump. The results, for example, when the tubing is surrounding at some point by a packing held by the casing or earth formation below the casing. In such wells the reagent may be introduced into the tubing through a pressure equalizing vessel, after stopping the flow of fluids. After being so treated, the well should be left closed in for a period of time sufficient to permit the reagent to drop to the bottom of the well.

For injection into the well annulus, the corrosion inhibitor is usually employed as a solution in a suitable solvent. The selection of solvent will depend much upon the exact reagent being used and its solubility characteristics.

For treating wells with packed-off tubing, the use of solid "sticks" or plugs of inhibitor is especially convenient. These may be prepared by blending the inhibitor with a mineral wax, asphalt or resin in a proportion sufficient to give a moderately hard and high-melting solid which can be handled and fed into the well conveniently.

The protective action of the herein described reagents appears to be maintained for an appreciable time after treatment ceases, but eventually is lost unless another application is made.

For the protection of gas wells and gas-condensate wells, the amount of corrosion inhibitor required will be within range of one-half to 3 lbs. per million cubic feet of gas produced, depending upon the amounts and composition of corrosive agents in the gas and the amount of liquid hydrocarbon and water produced. However, in no case does the amount of inhibitor required appear to be stoichiometrically related to the amount of acids produced by a well, since protection is obtained with much less corrosion inhibitor than usually would be required for neutralization of the acids produced.

These compositions are particularly effective in the prevention of corrosion in systems containing a corrosive aqueous medium, and most particularly in systems containing brines.

These compositions can also be used in the prevention of corrosion in the secondary recovery of petroleum by water flooding and in the disposal of waste water and brine from oil and gas wells. Still more particularly, they can be used in a process of preventing corrosion in water flooding and in the disposal of waste water and brine from oil and gas wells which is characterized by injecting into an underground formation an aqueous solution containing minor amounts of the compositions of this invention, in sufficient amounts to prevent the corrosion of metals employed in such operation.

When an oil well ceases to flow by the natural pressure in the formation and/or substantial quantities of oil can no longer be obtained by the usual pumping methods, various processes are sometimes used for the treatment of the oil-bearing formation in order to increase the flow of oil. These processes are usually described as secondary recovyry processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

We have now discovered a method of preventing corrosion in systems containing a corrosive aqueous media, and most particularly in systems containing brines, which is characterized by employing the compounds described herein.

We have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation an aqueous solution of the compositions of this invention.

The invention, then is particularly concerned with preventing corrosion in a water flooding process characterized by the flooding medium, containing an aqueous or an oil field brine solution of these compositions.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of these compositions, sufficient to prevent corrosion.

While the flooding medium employed in accordance with the present invention contains water or oil field brine and the compounds of this invention, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc. and in conjunction with other secondary recovery methods.

The concentration of the corrosion inhibitors of this invention will vary widely depending on the particular composition, the particular system, etc. Concentrations of at least about 5 p.p.m., such as about 10 to 10,000 p.p.m. for example about 25 to 5,000 p.p.m., advantageously about 50 to 1,000 p.p.m., preferably about 75-250 p.p.m. may be employed. Larger amounts can also be employed such as 1.5-5.0% although there is generally no commercial advantage in so doing.

For example, since the success of a water flooding operation manifestly depends upon its total cost being less than the value of the additional oil recovered from the oil reservoir, it is quite important to use as little as possible of these compounds consistent with optimum corrosion inhibition. Since these compounds are themselves inexpensive and are used in low concentrations, they enhance the success of a flood operation by lowering the cost thereof.

By varying the constituents of the composition, the compounds of this invention can be made more oil or more water soluble, depending on whether the compositon is to be employed in oil or water systems.

USE IN ACID SYSTEMS

The compositions of this invention can also be employed as corrosion inhibitors for acid systems, for example as illustrated by the pickling of ferrous metals, the treatment of calcareous earth formations, etc., as described in the following sections.

USE AS PICKLING INHIBITORS

This phase of the invention relates to pickling. More particularly, the invention is directed to a pickling composition and to a method of pickling ferrous metal. The term "ferrous metal" as used herein refers to iron, iron alloys and steel.

To prepare ferrous metal sheet strip, etc., for subsequent processing, it is frequently desirable to remove oxide coating, formed during manufacturing, from the surface. The presence of oxide coating, referred to as "scale" is objectionable when the material is to undergo subsequent processing. Thus, for example, oxide scale must be removed and a clean surface provided if satisfactory results are to be obtained from hot rolled sheet and strip in any operation involving deformation of the product. Similarly, steel prepared for drawing must possess a clean surface and removal of the oxide scale therefrom is essential since the scale tends to shorten drawing-die life as well as destroy the surface smoothness of the finished product. Oxide removal from sheet or strip is also necessary prior to coating operations to permit proper alloying or adherence of the coating to the ferrous metal strip or sheet. Prior to cold reduction, it is necessary that the oxide formed during hot rolling be completely removed to preclude surface irregularities and enable uniform reduction of the work.

The chemical process used to remove oxide from metal surfaces is referred to as "pickling." Typical pickling processes involve the use of aqueous acid solutions, usually inorganic acids, into which the metal article is immersed. The acid solution reacts with the oxides to form water and a salt of the acid. A common problem in this process is "overpickling" which is a condition resulting when the ferrous metal remains in the pickling solution after the oxide scale is removed from the surface and the pickling solution reacts with the ferrous base metal. An additional difficulty in pickling results from the liberated hydrogen being absorbed by the base metal and causing hydrogen embrittlement. To overcome the aforementioned problems in pickling, it has been customary to add corrosion inhibitors to the pickling solution.

The present invention avoids the above-described problems in pickling ferrous metal articles and provides a pickling composition which minimizes corrosion, overpickling and hydrogen embrittlement. Thus the pickling inhibitors described herein not only prevent excessive dissolution of the ferrous base metal but effectively limit the amount of hydrogen absorption thereby during pickling. According to the invention, a pickling composition for ferrous metal is provided which comprises a pickling acid such as sulfuric or hydrochloric acid and a small but effective amount of the dithiol thione compound of this invention, for example at least about 5 p.p.m., such as from about 100 to 5,000 p.p.m., but preferably from about 500 to 1,500 p.p.m.

Ferrous metal articles are pickled by contacting the surface (usually by immersion in the pickling solution) with a pickling composition as described to remove oxide from their surface with minimum dissolution and hydrogen embrittlement thereof and then washing the ferrous metal to remove the pickling composition therefrom.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oilbearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow or petroleum to the producing well.

USE AS CORROSION INHIBITORS IN DEEP WELLS

Because of the world wide shortage of petroleum products, deeper wells are now being drilled to tap new petroleum fields. However, increased depth poses more severe corrosion problems. For example as one drills to depths in excess of 10,000 ft., one encounters temperatures in excess of about 200° F., such as from about 200° to 550°, for example from about 250° to 550°, but generally within range of about 300° to 450°; pressures in excess of about 5,000 psi, such as from about 5,000 to 40,000, for example from about 7,500 to 30,000, but generally in the range of about 8,000 to 20,000; and high acidity, particularly that due to $H_2S$, $CO_2$, etc., for example $H_2S$ or $CO_2$ partial pressures of acidic gases in excess of about 10 psi, such as from about 10 to 20,000, for example from about 100 to 10,000, but generally from about 200 to 5,000.

These partial pressures of acidic gases can be obtained by analysis of $H_2S$ or $CO_2$ in the range from a few p.p.m. to 80%, for example from 1,000 p.p.m. to 50%, but generally from 2% to 40%.

Conditions as extreme as these, place great corrosive stress upon the tubing employed in such wells. Thus, when drilling such wells costs in excess of $5-$6 million dollars, approximately half of which is tubing, the importance of effective corrosion inhibition is evident. However, when conventional oil well corrosion inhibitors are employed they are found to be of little or no effectiveness since they tend to degrade, volatilize, polymerize, and either lose effectiveness as corrosion inhibitors or polymerize so as to clog the tubing.

We have further discovered that these compositions are effective as corrosion inhibitors in systems of high temperature, high pressure and high acidity, particularly in deep wells, and most particularly in deep gas wells.

In order to compare the sulfur-amino compositions of this invention with corresponding non-sulfur amino compositions, the following non-sulfur amino compositions were prepared and tested as corrosion inhibitors.

EXAMPLE 38

To aminoethylethanolamine (52 g; 0.5 mole) was added methyl acrylate (43 g; 0.5 mole) dropwise in 30 min. while cooling to maintain a temperature below 50° C. After completing the addition the reaction was heated with stirring to 180°–185°. As the temperature reached 135° methanol began to be produced and was collected (15 g). Heating was terminated after 4 hrs. yielding a viscous product soluble in water

EXAMPLE 39

By the method of Example 38 methyl acrylate (43 g; 0.5 mole) and diethylene triamine (52 g; 0.5 mole) were condensed until methanol (15 g) had been collected. The product 77 g was obtained as a viscous dark yellow liquid readily soluble in water.

EXAMPLE 40

Following the procedure of Example 38 methyl methacrylate (50 g; 0.5 mole) was reacted with ethylenediamine (60 g; 1.0 mole). After removal of methanol of condensation and some excess ethylene diamine the product was obtained as a dark viscous oil soluble in water.

EXAMPLE 41

To diethylene triamine (52 g; 0.5 mole) cooled in an ice bath was added acrylonitrile (30 g; 0.56 mole) in 40 min. at <60° C. Upon completion of this addition thiourea (0.8 g) was added as catalyst and the mixture heated to 150°–165°. Ammonia evolution proceeded rapidly and was complete after 4 hours. Upon cooling a viscous brown product was obtained readily soluble in water.

EXAMPLE 42

Following the procedure of Example 41 aminoethylethanolamine (52 g; 0.5 mole) was condensed with acrylonitrile (30 g; 0.56 mole) in presence of thiourea as catalyst. The viscous product was water soluble

EXAMPLE 43

Lauric acid (40 g; 0.2 mole) and aminoethylethanolamine (20.1 g; 0.2 mole) were heated in xylene (200 ml) in a flask fitted with Dean Stark tube. As the solution was heated at reflux water of condensation was collected. After 12 hrs. 7 ml of water had been collected and the reaction was complete. The product showed infrared absorption consistent with the imidazoline structure expected as shown below:

$$\begin{array}{c} CH_2-CH_2 \\ N \diagup \quad \diagdown NCH_2CH_2OH \\ \diagdown \diagup \\ C \\ | \\ C_{11}H_{23} \end{array}$$

Corrosion Test Results

Corrosion tests were carried out at ambient temperature in 2% sodium chloride saturated with carbon dioxide. Corrosion rates were measured using PAIR meter of the type described in U.S. Pat. No. 3,406,101. Inhibitors were injected after the electrodes had been allowed to corrode for 2 hours.

Protection is calculated in the usual manner from corrosion rate ($R_1$) of fluids without inhibitor and corrosion rate ($R_2$) in presence of particular inhibitor according to the formula:

$$\frac{R_1 - R_2}{R_1} \times 100 = \text{Percent protection.}$$

Blank corrosion rates under these conditions was 51 mpy.

TABLE 4

| | Corrosion Test Data | | | |
|---|---|---|---|---|
| | Percent Protection at Concentration | | | |
| Example | 5 ppm | 25 pm | 50 ppm | 100 ppm |
| Example 1 | — | 88 | 96 | — |
| Example 3 | — | 49 | 57 | 87 |
| Example 5 | — | — | 71 | 92 |
| Example 6 | — | 36 | — | 74 |
| Example 7 | 61 | 97 | 98 | 99 |
| Example 19 | — | 65 | 91 | 96 |
| Example 21 | — | 59 | — | 90 |
| Example 27 | — | 82 | 80 | — |
| Example 28 | — | — | 73 | — |
| Example 29 | — | — | 70 | — |
| Example 41 | — | 0 | 0 | — |
| Example 42 | — | 0 | — | — |
| Example 43 | — | 15 | — | — |

Acid Inhibitors test in Hydrochloric Acid 200 ml of 5% hydrochloric acid in a 300 ml beaker is heated to 165°–170° F. and the chemical to be tested is added at the appropriate concentration. Cleaned 1020 mild steel coupons (7/8×3¼×1/6″) are weighed and then placed in the acid for exactly one hour. The coupons are removed and washed with hot water, hot acetone, air dried and then re-weighed.

Corrosion protection is calculated in the usual manner from the weight loss of the blank ($W_1$) and weight loss ($W_2$) in the presence of inhibitor according to the formula $$\frac{W_1 - W_2}{W_1} \times 100 = \text{Percent protection}.$$

The coupons used in corrosion experiments weighed 20.5–21 g and the typical weight loss without inhibitors was 1.3 g.

TABLE 5
Pickle Acid Inhibitor Tests

| Compound | Concentration pm | Protection |
|---|---|---|
| Example 1 | 250 | 95% |
| Example 2 | 250 | 95% |
| Example 5 | 250 | 93% |
| Example 6 | 250 | 89% |
| Example 7 | 250 | 95% |
| Example 8 | 250 | 94% |
| Example 13 | 250 | 92% |
| Example 14 | 250 | 92% |
| Example 19 | 250 | 96% |
| Example 24 | 250 | 95% |
| Example 25 | 250 | 76% |
| Example 26 | 250 | 74% |
| Example 33 | 250 | 94% |
| Example 35 | 250 | 92% |
| Example 36 | 250 | 96% |
| Example 42 | 250 | 77% |

We claim:

1. A process of inhibiting corrosion which is characterized by treating a metal with a composition of the following formula:

$$\text{RS:CH}_2\text{—CH(OH)—CH}_2\text{:}\widehat{N}$$

where $R_1$ is a hydrocarbon group, having 1 to 14 carbon atoms and $\widehat{N}$ is an amino moiety, where the molar ratios of $$\text{RS:CH}_2\text{CH(OH)—CH}_2\text{:}\widehat{N}$$

are other than 1:1:1.

2. A process of inhibiting corrosion which is characterized by treating a metal with the composition of claim 1 where $$\widehat{N} \text{ is } N\diagup^{R_2}_{\diagdown R_4}\!\!-R_3$$

where $R_2$, $R_3$ and $R_4$ are H, alkyl, aryl, or $$-[\text{alkylene}-\overset{H}{N}-]_n-H,$$

and where n is 1 or more; where the molar ratios of $$\text{RS:CH}_2\text{CH(OH)—CH}_2\text{:}\widehat{N}$$

are other than 1:1:1.

3. A process of inhibiting corrosion which is characterized by treating metal with the composition of claim 1 where the molar ratios are as follows:

$$\text{RS:CH}_2\text{—CH(OH)—CH}_2\text{:}\widehat{N}$$

from about 0.05:0.9:1 to 0.05:0.05:1.

4. A process of inhibiting corrosion which is characterized by treating a metal with the composition of claim 2 where the molar ratios are as follows $$\text{RS:CH}_2\text{—CH(OH)—CH}_2\text{:}\widehat{N}$$

from about 0.2:0.8:1 to 0.5:0.5:1.

5. A process of inhibiting corrosion which is characterized by treating a metal with the composition of claim 2 where the ratios of $$\text{RS:CH}_2\text{—CH(OH)—CH}_2\text{:N}\diagup^{R_2}_{\diagdown R_4}\!\!-R_3$$

are as follows: from about 0.05:0.9:1 to 0.05:0.05:1.

6. A process of inhibiting corrosion which is characterized by heating a metal with the composition of claim 2 where the ratios of $$\text{RS:CH}_2\text{—CH(OH)—CH}_2\text{:N}\diagup^{R_2}_{\diagdown R_4}\!\!-R_3$$

are as follows: from about 0.2:0.8:1 to 0.5:0.5:1.

7. A process of inhibiting corrosion which is characterized by treating a metal with the composition of claim 2 having the formula:

$$\text{CH}_3(\text{CH}_2)_n\text{S CH}_2\text{CH(OH)—CH}_2\oplus\text{—N}^R_R[\text{—(CH}_2)_m\text{—N}^H]_p\text{—H} \quad X^\ominus$$

R=H or alkyl, X-anion, n, m, p are 1 or more.

8. A process of inhibiting corrosion which is characterized by treating a metal with the composition of claim 2 where the molar ratios of $$\text{CH}_3(\text{CH}_2)_n\text{S:CH}_2\text{—CH(OH)—CH:N}^R_R[(\text{CH}_2)_m\text{—N}^H]_p\text{—H}$$

are as follows: from about 0.05:0.9:1 to 0.05:0.05:1.

9. A process of inhibiting corrosion which is characterized by treating a metal of claim 7 where the molar ratios of $$\text{CH}_3(\text{CH}_2)_n\text{S:CH}_2\text{—CH(OH)—CH:N}^R_R[(\text{CH}_2)_m\text{—N}^H]_p\text{—H}$$

are as follows: from about 0.05:0.8:1 to 0.5:0.5:1.

* * * * *